United States Patent
Brown et al.

(10) Patent No.: US 9,308,489 B2
(45) Date of Patent: *Apr. 12, 2016

(54) ADSORPTION PROCESS FOR THE DEHYDRATION OF ALCOHOL

(71) Applicant: Thermal Kinetics Systems, LLC, Amherst, NY (US)

(72) Inventors: Christopher Brown, Buffalo, NY (US); Marion Simo, Kenmore, NY (US)

(73) Assignee: Thermal Kinetics Systems, LLC, Amherst, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/558,655

(22) Filed: Dec. 2, 2014

(65) Prior Publication Data

US 2015/0290579 A1    Oct. 15, 2015

Related U.S. Application Data

(63) Continuation of application No. 13/499,940, filed as application No. PCT/US2010/047918 on Sep. 3, 2010, now Pat. No. 8,901,359.

(60) Provisional application No. 61/239,585, filed on Sep. 3, 2009.

(51) Int. Cl.
 *C07C 29/76* (2006.01)
 *B01D 53/26* (2006.01)
 *B01D 53/047* (2006.01)

(52) U.S. Cl.
 CPC ............ *B01D 53/261* (2013.01); *B01D 53/047* (2013.01); *C07C 29/76* (2013.01); *B01D 2256/00* (2013.01); *B01D 2257/80* (2013.01)

(58) Field of Classification Search
 CPC ...................................................... C07C 29/76
 USPC ........................................................... 568/916
 See application file for complete search history.

(56) References Cited

U.S. PATENT DOCUMENTS 8,901,359 B2 * 12/2014 Brown et al. .................. D53/47

* cited by examiner

*Primary Examiner* — Elvis O Price
(74) *Attorney, Agent, or Firm* — Bond Schoeneck & King

(57) ABSTRACT

The present invention includes a process for the dehydration of ethanol by adsorption of water at elevated pressure and for the regeneration (purging) of adsorbent at a lower pressure than the pressure used for the adsorption of water where the ratio of the duration of the regeneration (purge) step to the duration of the water adsorption step is higher than 0.1 and the temperature of adsorption is greater than 260 degree Fahrenheit.

10 Claims, 3 Drawing Sheets

Figure 2: 3A Adsorption Isotherm Data

ADSORPTION PROCESS FOR THE DEHYDRATION OF ALCOHOL

CROSS REFERENCE TO RELATED APPLICATION

This application is a continuation of U.S. application Ser. No. 13/449,940 filed Sep. 26, 2012, now pending, which is a 371 of PCT Application No. PCT/US10/47918 filed Sep. 3, 2010, now expired, which claims the benefit of U.S. Prov Appl. No. 61/239,585 filed Sep. 3, 2009, now expired. All of these prior applications are incorporated herein by reference in their entirety.

FIELD OF THE INVENTION

This invention relates to the improvement of current adsorption process used for the alcohol dehydration in terms of new process arrangement and operation.

BACKGROUND OF THE INVENTION

Lower alcohols (i.e. C 1-4 alcohols) are important components as reactants in a wide range of chemical processes and as a fuel source. Ethanol has been mandated by the United States government as a gasoline additive and/or as a major component of automobile fuel. The use of ethanol as a fuel additive has been gaining popularity because it is renewable and is a cleaner burning fuel source than most components of gasoline. Particularly, production of ethanol worldwide has been steadily increasing over the past years. Ethanol is usually produced by a fermentation process. The fermentation broth, typically containing 5 wt. % to 13 wt. % ethanol, is distilled to increase the ethanol content beyond 90 wt. % and requires purification to greater than 99 wt. % to be useful as fuel grade alcohol.

Due to the existence of the ethanol-water azeotrope at a concentration of about 95 wt. % ethanol, further ethanol concentration is accomplished using azeotropic distillation or by adsorption separation process such as a pressure swing adsorption (pressure swing adsorption) process. The dry ethanol stream preferably has less than 0.5% moisture content to meet the criteria for blending with gasoline. Azeotropic distillation requires the use of benzene to break the azeotrope. Because of the carcinogenic nature of benzene, other efficient separation techniques are desirable.

Pressure Swing Adsorption (PSA) is a separation process for selectively separating one component ("target component") from of a liquid mixture. The target component is selectively adsorbed onto a solid adsorbent under relatively high pressure. At that pressure the other components are not adsorbed or is weakly adsorbed onto the solid adsorbent. After the capacity of the adsorbent to adsorb the target component is exhausted, the adsorbent is regenerated. Regeneration occurs by reducing the partial pressure of the target component in the adsorbent bed. This is accomplished by lowering the total pressure of the vapor in the adsorption bed and/or by passing a purge gas over the solid adsorbent. The target component is released by this combination of pressure reduction and purge from the solid adsorbent into the purge stream. The adsorbent bed is then re-pressurized and has a regenerated capacity to adsorb more of the target component onto the surface of the solid adsorbent.

The original pressure swing adsorption cycle was invented by Skarstrom in 1960 (See U.S. Pat. No. 2,944,627). According to Skarstrom, the two steps of adsorption and regeneration (or purge step) are carried out in two adsorbent beds operated in tandem, enabling the processing of a continuous feed. Since the introduction of the Skarstrom cycle, many more sophisticated pressure swing adsorption processes have been developed and commercialized. Such processes have attracted increasing interest more recently because of their low energy requirements and low capital investment costs.

One of the earliest disclosures of removing water (target component) from ethanol by pressure swing adsorption is found in U.S. Pat. No. 2,137,605 ("Derr"). Derr describes a method that uses freshly reactivated alumina to adsorb the moisture.

U.S. Pat. No. 4,465,875 ("Greenbank") and U.S. Pat. No. 4,407,662 ("Cinder") describe the use of molecular sieves to dry the ethanol. U.S. Pat. No. 4,273,621 ("Fornoff") describes a process for the ethanol dehydration in the presence of carbon dioxide using a crystalline zeolite having a pore size of 3 Angstroms with high affinity for water. The 3 angstrom pore size is highly selective because the binding site for water is within a pore that is large enough to permit water to enter into the pore, but is too small to allow ethanol to enter the pore.

United States Patent Application 20070000769 ("Brown I") incorporated by reference in its entirety discloses a process for producing fuel grade alcohol from a fermentation process that includes use of pressure swing adsorption. PCT Publication No. WO 2010/096626 ("Brown II") discloses the use of pressure swing adsorption in a process for recovery of methanol.

Common feature for all pressure swing adsorption ethanol dehydration cycles encountered in the industry today is the low value of the ratio of the purge time to the adsorption time—often about 0.05 or less. The other previously unsolved constraint of the current-state-of-the-art is that the rate of the blowdown and the pressurization step is limited to ~25 Psia/min. A faster rate will make the bed particles fluidize and thus cause irreversible damage to the adsorbent material.

Thus, there is a need for a system of operation of an adsorption bed for separation of water from lower alcohols that has a greater volume output without compromising purity, an improvement in purity without compromising output, a reduction in the blowdown or pressurization time without increasing the loss of adsorbent. The present invention addresses these and other needs.

SUMMARY OF THE INVENTION

The present invention includes a process for the dehydration of C 1-4 alcohol that increases the productivity or performance of existing adsorption beds, particularly pressure swing adsorption beds. The present invention provides fuel ethanol production facilities with increased ethanol yield. With low operation pressure, less ethanol is used in regeneration. Additionally, the present invention provides protection against bed lift during depressurization and faster regeneration resulting from a bed design that introduces the alcohol feedstream from the bottom of adsorption bed. The present invention facilitates better interface with distillation resulting from increased re-pressurization time which provides steadier flow of dried alcohol product. The quality of bed regeneration is improved which improves the dried alcohol yield and bed drying capacity.

In one embodiment, the system allows better interface with downstream operations recovering heat from the dehydrated ethanol stream.

In one embodiment, there is a process for the dehydration of a C 1-4 alcohol comprising the steps of: (1) providing an adsorption bed having an adsorbent material; (2) first contacting a feedstream comprising C 1-4 alcohol and water at a temperature above 260 F with an adsorption bed at a first pressure for an adsorption phase time to produce a dehydrated alcohol stream; (3) reducing the pressure of the adsorption bed to a second pressure for a blowdown phase time; (4) second contacting the dehydrated alcohol stream with the adsorption bed for a purge phase time at a second pressure wherein the ratio of the purge phase time to an adsorption phase time is greater than 0.1; and increasing the pressure of the adsorption bed to the first pressure for a pressurization phase time.

In one embodiment, the adsorption bed has a top end and a bottom end and the feedstream enters the adsorption bed from the bottom of the bed and the purge stream enters the adsorption bed from the top of the bed.

In another embodiment, there is a process for the dehydration of ethanol. The process includes providing an adsorption bed having a water adsorbent material. A feedstream comprising C1-4 alcohol and water is contacted at a temperature above 260 degrees F. with an adsorption bed at a first pressure for an adsorption phase time to produce a dehydrated alcohol stream. The feedstream enters the bed from an inlet at the bottom of the adsorption bed. The pressure of the adsorption bed is reduced to a second pressure for a blowdown phase time. The dehydrated alcohol stream is contacted with the adsorption bed for a purge phase time at the second pressure. The pressure of the adsorption bed is increased to the first pressure for a pressurization phase time. The cycle is repeated.

In one embodiment, the ratio of purge phase time to the adsorption phase time is greater than 0.2, preferably greater than 0.3, more preferably greater than 0.5 and optimally between 0.5 and 1.0.

In another embodiment, the step of providing provides two, three or four adsorption beds in a pressure swing adsorption system—preferably two beds in the system.

In still another embodiment, the feedstream temperature is greater than 260 degrees Fahrenheit, preferably greater than 300 degrees Fahrenheit, more preferably greater than 320 degrees Fahrenheit.

In still another embodiment, the ratio of first pressure to second pressure is greater than 10. In another embodiment the pressure swing adsorption system is a pressure vacuum swing adsorption system. Optionally, the feed pressure is less than 25 psia (preferably less than 20 psia) and the reduced pressure for blowdown is less than 2.5 psia (preferably less than 2 psia).

In still another embodiment, the dehydrated alcohol stream produces an exhaust stream that is directed to a distillation column.

In yet another embodiment, the feedstream comprises less than 10 wt. % water.

Optionally, the step of reducing pressure and the step of increasing pressure has a rate of pressure change that is greater than 30 psi per minute and preferably greater than 50 psi/minute.

Alternatively, the adsorbent has a pore size larger than the average diameter of a water molecule but smaller than the average diameter of the alcohol. Preferably, the pore size is less than 4 angstroms, most preferably about 3 angstroms. Optionally, the molecular sieve is a 3 angstrom zeolite molecular sieve catalyst available from various suppliers.

In one embodiment, the C1-4 alcohol is methanol or ethanol. In another embodiment, the C 1-4 alcohol is ethanol.

DETAILED DESCRIPTION OF THE INVENTION

Definitions

Figure 1:
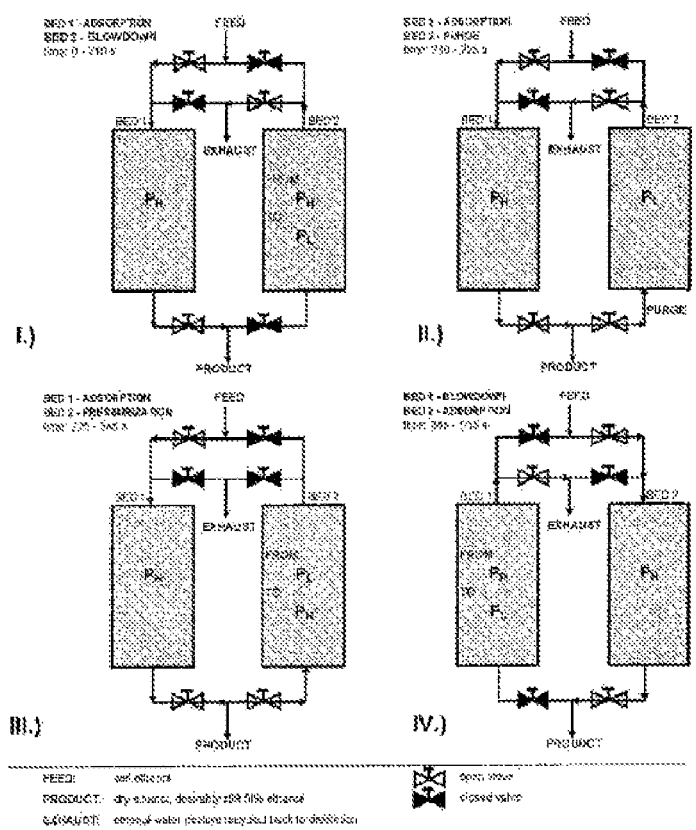
FIG. 1 is a schematic of a two-bed pressure swing adsorption system illustrating the four stages of a pressure swing adsorption cycle which can be operated with more efficiency according to one embodiment of the present invention.

"C 1-4 alcohol" is a hydrocarbon alcohol having one to four hydrocarbons in each molecule. For example ethanol is a C 2 hydrocarbon.

"Dehydration" is the selective removal of water from a composition resulting in a composition having a lower water content after dehydration. Dehydration of alcohol involves separation of water from a primary alcohol stream.

"Adsorption bed" is a bed of solid material that selectively binds to at least one component in a multi component system over at least one or more other components in that system.

"Feedstream" as used in the present invention is the stream containing alcohol and water that is processed to remove all or a portion of the water in a pressure swing adsorption system.

"Adsorption phase," as used in this invention is the phase where feedstream is passed through a bed in the pressure swing adsorption system to remove water at a pressure that favors the selective adsorption of water onto the adsorbent in the system.

"Blowdown phase" is the phase typically following the adsorption phase where the pressure is reduced from the adsorption pressure to a lower pressure that favors removal of the alcohol from the adsorbent.

"Regeneration phase" or "purge phase" is the phase that typically follows the blowdown phase where the partial pressure of water is sufficiently low to favor the separation of water from the adsorbent.

"Pressurization phase" is the phase that typically follows the regeneration phase where the pressure is increased from the regeneration pressure to the adsorption pressure.

"Purge stream" is a stream that passed through and adsorption bed during the regeneration phase to aid in the separation of water from the adsorbent.

"Exhaust stream" is a stream that removes gas from the adsorbent bed during the blowdown phase, and purge phase.

Improved Pressure Swing Adsorption Process

Without being limited to a particular theory of operation, experimental and mathematical modeling studies of the ethanol dehydration pressure swing adsorption process have revealed that by increasing the duration of the purge step ($t_{PURGE}$) the ratio $t_{PURGE}/t_{ADS}$ will be increased and the pressure swing adsorption unit will have improved performance including: (1) better product quality without increased operating cost; (2) higher throughput while delivering the product of the same quality (eg. 99.5% pure dry ethanol in one embodiment) or (3) reducing capital expenses by using a smaller pressure swing adsorption system to accomplish the same standard of drying that could previously be obtained with a larger system. However, these benefits are non-limiting as there are more variables that can affect the performance of a pressure swing adsorption unit. For example one could increase the purge flow rate while keeping the $t_{PURGE}$ constant.

A more general operating parameter is defined in order to capture the idea of our invention:

$$\frac{P}{F} = \frac{\text{Volume of Purge}}{\text{Volume of Feed}} = \frac{t_{PURGE} \times \dot{V}_P}{t_{ADS} \times \dot{V}_F} = \frac{t_{PURGE} \times \dot{F}_P \times P_H}{t_{ADS} \times \dot{F}_F \times P_L},$$

where duration of steps was defined previously, $V_F$ and $V_P$ correspond to the volumetric flow rate of the feed and purge, respectively (both in actual volume units). After rearrangement and introduction of molar flow rates of the purge ($F_P$) and the feed ($F_F$) and the operating pressures we get the definition of P/F ratio (purge to feed ratio).

This ratio is often utilized to characterize the operation of a pressure swing adsorption process. The recommended value for the efficient operation is usually close to unity. However, the value characterizing the operation of current ethanol pressure swing adsorption process is close to 0.07. It is one object of the present invention to operate the ethanol dehydration pressure swing adsorption unit with higher values of P/F ratio than currently used.

The definition of physically meaningful cycle requires that the condition $t_{ADS} = t_{BLOW} + t_{PURGE} + t_{PRES}$ is satisfied. To increase the P/F ratio, while keeping the flows and pressures constant, the following expression needs to be maximized:

$$\frac{t_{PURGE}}{t_{ADS}} = \frac{t_{ADS} - t_{BLOW} - t_{PRES}}{t_{ADS}}$$

The higher the time required for the blowdown and pressurization steps is, the lower the value of P/F ratio is found. Thus, it is desirable to reduce the duration of blowdown and pressurization steps in order to increase the P/F ratio. Previously, pressure swing adsorption operating conditions were constrained to a rate of pressure change in the bed to less than 25 Psia/min. Pressurization rate above this would cause turbulence in the absorption bed. This in turn would cause the adsorption particles to break down (disintegrate) more rapidly. The disintegration would increase operating cost making operation above this threshold prohibitively expensive. In one embodiment, the flow in the pressure swing adsorption unit is reversed so that flow during the adsorption step is from the bottom to the top of the adsorption bed. In contrast, flow during the purge phase, blowdown phase and pressurization phase is from bottom to the top. Thus, by increasing the rate of blowdown, the blowdown and pressurization steps can occur more rapidly leaving more time in the desorption cycle to purge the adsorption system.

As a result, higher values of P/F ratio (closer to 1) can be achieved in the pressure swing adsorption unit.

Description of the present invention is made with reference to FIG. 1. An alcohol (eg. ethanol) dehydration process using the pressure swing adsorption system with 3A zeolite is illustrated. The ethanol dehydration pressure swing adsorption process utilizes two beds loaded with zeolite 3A. The three bed process is also used in the industry.

The below example have operating times that are a benchmark by which process changes can be illustrated to improve performance.

ADSORPTION: The wet ethanol stream (feed), of one embodiment, is introduced to the top of the bed at high pressure ($P_H$). The feedstream enters the bed and a product stream containing dry ethanol is withdrawn from the wet ethanol stream. Typically in one embodiment, pressure between 55 psia and 100 psia is used in the adsorption stage. These operating parameters correspond to operating at a temperature that is a minimum of 260 degrees Fahrenheit, preferably a minimum of 300 degrees Fahrenheit, most preferably a minimum of about 330 degrees Fahrenheit. Vapor flows downward through the bed. The water is being adsorbed and at the same time the high pressure dry ethanol product is withdrawn at the bottom of the bed. For a two bed system, the duration of adsorption step defines the half cycle time. The duration of the remaining steps (blowdown, purge and pressurization) together preferably equal to the duration of adsorption step. In the example of FIG. 1, the adsorption time of BED 1 is 345 seconds, while the BED 2 undergoes blowdown phase, purge phase and pressurization phase that total 345 seconds likewise. Afterwards the beds are switched and the sequence repeats itself.

BLOWDOWN: Blowdown is illustrated in FIG. 1 part I and part IV. The bed 2 in part I and bed 1 in part IV is depressurized from the relatively high pressure of part I to low the relatively low pressure of part II, typically 2.5 to 3.5 psia. The blowdown occurs by shutting off the feedstream to the bed and withdrawing the gaseous content of the bed through an exhaust stream until the desired pressure is reached. The exhaust stream is recycled back to downstream distillation process. As noted, the system described in FIG. 1 has a net fluid flow during the blowdown that is in the direction of the top of the adsorbent bed. Thus, a blowdown rate of pressure change cannot typically exceed 25 psia per minute. In one embodiment, the blowdown time is about 210 seconds and corresponds to an adsorption time of 345 seconds.

PURGE: The purge step is illustrated in FIG. 1 part II. Bed 2 is regenerated (purged) using a portion of dry ethanol from the product stream and cycling it into the bottom of Bed 2 for a period of time. While the example of FIG. 1 shows a system having a short purge time of 15 seconds with an adsorption time of 345 seconds, extending the adsorption time to 360 seconds, doubles the purge time (30 seconds) and greatly improves the product quality as illustrated in Example 1 below.

PRESSURIZATION: The pressurization step is shown in FIG. 1 part III. The pressure in Bed 2 is raised from $P_L$ to $P_H$ using a portion of the dry ethanol product stream. After the pressurization is complete the bed is ready to be switched to the adsorption step. The pressurization time in one non-limiting embodiment is 125 seconds. The pressurization rate is limited by the fact that the pressure change in the adsorbent bed cannot exceed 25 psia per minute without introducing destructive turbulent flow in the system.

Improvements in Operation

In one preferred embodiment, when operating at an adsorption pressure less than 40 psia and particularly less than 25 psia or 20 psia a greater product yield can be obtained by operating at a temperature that is greater than 260 degrees Fahrenheit, preferably 300 to 330 degrees Fahrenheit. The higher temperature for one, permits operating at relatively lower pressures as does developing higher purge volumes. The changes in temperature and pressure are permitted by operating at a higher P/F ratio.

Another preferred cycle reverses the flow of feedstream, exhaust and product through the adsorbent bed system so that flow during adsorption occurs from bottom of the beds upward and flow during the blowdown, purge and pressurization phases are downward. This permits more aggressive flow during the blowdown and pressurization phases and ultimately allows a longer purge time relative to adsorption and a greater P/F ratio. Adsorption occurs at 20 psia for 300 minutes; purge pressure is less than 1.8 psia with a blowdown time of 50 seconds, a purge time of 180 seconds, a pressurization time of 50 seconds. As a result a P/F ratio of between 0.5 and 1.0 is easily obtained.

The present invention entails the modifications of the current PSA cycle sequence and of the operation arrangement in a way that will allow the PSA unit to operate more efficiently. The key elements of this invention include 1) a significant purge time to aid in bed regeneration, 2) a hot wet feed vapor above 300 F flowing upwards through the adsorption bed, 3) a downward flow for depressurization and pressurization to allow shorter times for these steps, 4) a long purge time also in a downward flow and 5) as a consequence of better bed regeneration from 1 through 4 a lower adsorption pressure becomes possible allowing the potential use of waste heat for vaporization.

Figure 3:
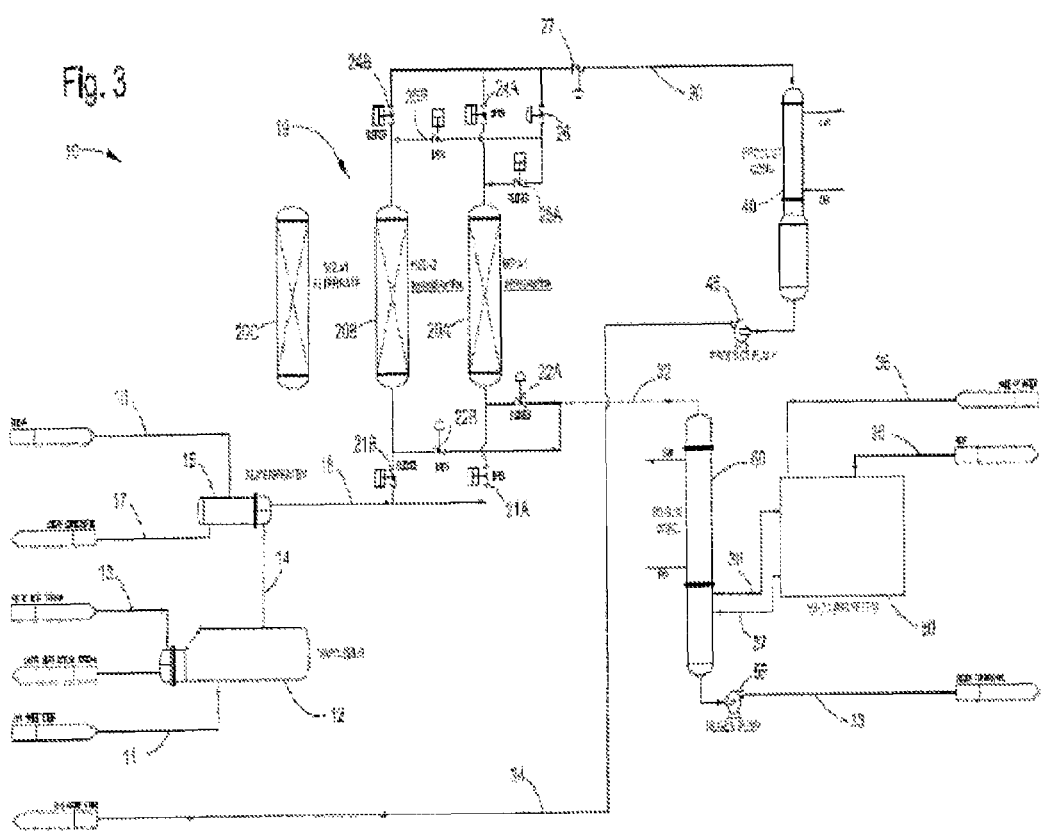
FIG. 3 is a schematic of a pressure swing adsorption system integrated with an ethanol distillation column according to one embodiment of the present invention.

With reference to FIG. 3, an ethanol drying system 10 is disclosed according to one embodiment of the present invention. It will be understood that this system can be modified to dry other alcohols, including alcohols that do not form azeotropes with water or do not form constant boiling mixtures with water. Thus, it is understood that any discussion relating to ethanol in the description of the schematic process in this specification may apply to other alcohols also. A wet ethanol feed stream 11 is vaporized in an ethanol vaporizer 12 heated by a waste heat stream 13 which may be in vapor or liquid form as long as ethanol feed stream 11 can be vaporized at a pressure above 18 psia. The vaporized ethanol is fed along a vaporized ethanol feed stream 14 to an ethanol superheater 15 which is heated by process steam supplied by steam feed 16 and withdrawn from the superheater steam condensate 17. The superheated ethanol feed steam 18 is fed into a pressure vacuum swing adsorption system 19. The pressure swing adsorption system 19 has a first molecular sieve unit 20A and a second molecular sieve unit 20B. Optionally, a third molecular sieve unit 20C may be included. However, for the sake of illustration, the fluid system is shown for a two-bed system only. A person of ordinary skill in the art will readily be able to adapt the flow diagram to accommodate a three-bed or greater bed number pressure swing adsorption system without undue experimentation.

While the first molecular sieve unit 20A is in a dehydration mode, the second molecular sieve unit 20B is in regeneration mode where the second molecular sieve unit 20B is first depressurized, then purged with the dry ethanol stream and finally re-pressurized. The adsorption time for each bed is generally from 4 to 10 minutes. For this example the time for operating one bed under adsorption and the time to fully regenerate the other bed will be taken as 5 minutes. During this part of the cycle, the first inlet valve 21A is open and the second inlet valve 21B is closed directing the vaporized wet methanol feed from line 18 into the first molecular sieve unit 20A. As the ethanol passes upwardly through the molecular sieve unit 20A, water is selectively adsorbed into the pores of the molecular sieve and the dry ethanol passes through a first product outlet valve 24A and master product outlet backpressure valve 27 along dry ethanol stream 30 and to product condenser 40. During the entire regeneration process, second product outlet valve 24B is closed to prevent flow of regenerate into the dry ethanol stream 30.

Under regeneration conditions, the second molecular sieve unit 20B is first depressurized in a downward flow in less than 50 seconds to approximately 1.0 to 1.5 psia. During depressurization, both the first purge inlet valve 25A and second purge inlet valve 25B are closed to prevent purge from entering the second molecular sieve unit 20B during depressurization. The first depressurization outlet valve 22A is closed to prevent flow of the wet ethanol feed steam 18 into the regenerate product line 32. The second depressurization outlet valve 22B is ramped open allowing flow from the second molecular sieve unit 20B along regenerate product line 32. The regenerate product will contain a mixture of ethanol and water. The regenerate product line is under a vacuum condition as a result of the vacuum system 50. Thus, regenerate product flows freely from the pressurized second molecular sieve unit 20B along the regenerate product line 32.

Once the second molecular sieve unit 20B is fully depressurized, the second purge inlet valve 25B is opened allowing a controlled flow of dry ethanol through control valve 26 to purge the water that is selectively adsorbed in the pores of the molecular sieve and withdraw such purge stream along regenerate product line 32 under vacuum conditions. This purge step will take 3 minutes in this example. Once the purge is completed for the second molecular sieve unit 20B, depressurization outlet valve 22B is closed while purge inlet valve 25B is increasingly open so that dry ethanol from first molecular sieve unit 20A can pressurize the second molecular sieve unit 20B in less than 50 seconds to the same pressure as the first molecular sieve unit 20A. An extra 20 seconds in the regeneration cycle is available for switching valves and for establishing a final equilibrium of pressures between the two molecular sieve beds.

Dehydration begins for the second molecular sieve unit 20B with the following valve arrangement. The second depressurization outlet valve 22B remains closed. The second purge inlet valve 25B is closed. The second product outlet valve 24B is opened, and the first inlet valve 21B is opened to facilitate flow from the vaporized wet methanol feed 18 into the second molecular sieve unit 20B and flow of dried ethanol from the second molecular sieve unit 20B through second product outlet valve 24B and master product outlet backpressure valve 27 into dry ethanol stream 30. The regeneration process as described above for the second molecular sieve unit 20B is repeated for the first molecular sieve unit 20A.

Preferably, the regeneration occurs at a pressure below atmospheric pressure under a vacuum created by the vacuum system 50. The regenerate leaves the second molecular sieve unit 20B as a vapor stream. It is cooled in a regenerate condenser 60 supplied by a cooling water source designated CWS.

Condensed regenerate product comprising mixed water and ethanol is withdrawn along stream 33 by regeneration pump 55 and returned to other processes in the plant. Condensed dry ethanol from product condenser 40 is withdrawn along stream 34 by product pump 45 and further cooled and sent to storage. The vacuum system includes a water make 35 up to assist in the vacuum operation and to control the concentration of ethanol in the regeneration condensate 33 and also includes a vent stream 36 to remove leakage air entering the vacuum. Vacuum system condensate 37 is returned to the regeneration condenser 60 while non-condensed vapor and air 38 is sent from the regeneration condenser 60 to vacuum system 50.

EXAMPLE 1

This example shows how the change in the P/F ratio can be increased by increasing the purge step and adsorption step duration while keeping the other variables constant. The values from the pressure swing adsorption process described in FIG. 1 were used for illustration.

TABLE 1

|  | OLD PROCESS | NEW PROCESS |
|---|---|---|
| $t_{ADS}$ [s] | 345 | 360 |
| $t_{BLOW}$ [s] | 210 | 210 |
| $t_{PURGE}$ [s] | 15 | 30 |
| $t_{PRES}$ [s] | 120 | 120 |
| $t_{PURGE}/t_{ADS}$ | 0.043 | 0.083 |
| Product [wt % EtOH] | 99.48% | 99.68% |

Only a 15 seconds increase in the purge step duration doubles the P/F ratio and as a result the quality of produced ethanol was improved.

EXAMPLE 2

This example illustrates how the reverse flow operation (feeding from the bottom of the bed) of the ethanol pressure swing adsorption unit affects the P/F ratio and eventually the final product quality. Virtually 100% dry product can be produced by this simple adjustment of the process arrangement. By assuming the rate of pressure change in the blowdown and pressurization step 53 Psia/min, an order of magnitude increase in the P/F ratio is observed, see Table 2. Alternative option to exploit this benefit will be to operate with higher feed flow rate and thus increasing the productivity of the pressure swing adsorption process (kg of EtOH/hr/kg of zeolite).

TABLE 2

|  | OLD PROCESS | NEW PROCESS |
|---|---|---|
| $t_{ADS}$ [s] | 345 | 345 |
| $t_{BLOW}$ [s] | 210 | 60 |
| $t_{PURGE}$ [s] | 15 | 225 |
| $t_{PRES}$ [s] | 120 | 60 |
| $t_{PURGE}/t_{ADS}$ | 0.043 | 0.652 |
| Pressure change rate, Psia/min | 25 | 53 |
| Product [wt % EtOH] | 99.48% | 99.999% |

Figure 2:
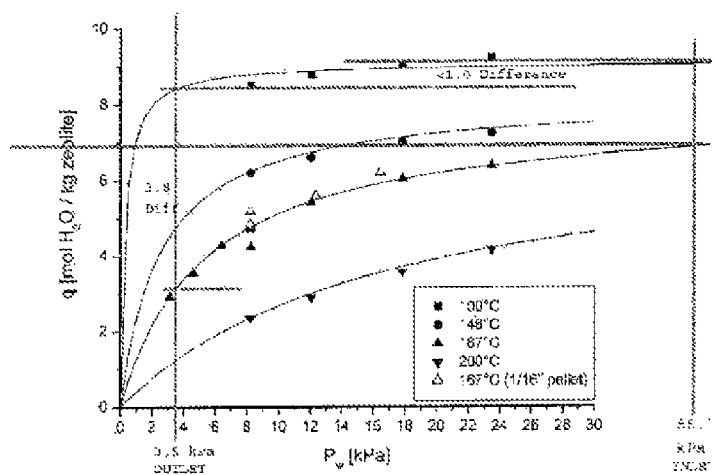
FIG. 2 is a chart showing adsorption isotherm data for a 3 angstrom zeolite catalyst.

Our experiments and data development for PVSA operations with 3A Zeolite have established an optimal temperature range for use in design of these systems in alcohol dehydration. The following chart illustrates the point:

The molar adsorption of 3A Zeolite, based on direct experimental data we have collected demonstrates and proves that operation at 167 C (332 F) is far superior to the lower temperature specified by Ginder. The adsorptive capacity as shown above is 3.8 times for 167 C (322 F) compared to 100 C (212 F). FIG. 2 shows the equilibrium water content of the Zeolite at 55 kPa partial pressure (inlet conditions) and 3.5 kPa partial pressure (outlet conditions). The difference between the two pressures determines the overall Zeolite adsorptive capacity and this pertains to any total pressure operation of adsorption and desorption.

What is claimed is:

1. A process for the dehydration of a C 1-4 alcohol comprising the steps of:
    providing an adsorption bed having an adsorbent material;
    first contacting a feedstream comprising C 1-4 alcohol and water at a temperature above 260 degrees Fahrenheit with an adsorption bed at a first pressure for an adsorption phase time to produce a dehydrated alcohol stream;
    reducing the pressure of the adsorption bed to a second pressure for a blowdown phase time;
    second contacting the dehydrated alcohol stream with the adsorption bed for a purge phase time at a second pressure wherein the ratio of the purge phase time to an adsorption phase time is greater than 0.1; and
    increasing the pressure of the adsorption bed to the first pressure for a pressurization phase time
    wherein the adsorption bed has a top end and a bottom end and the feedstream enters the adsorption bed from the bottom of the bed and the purge stream enters the adsorption bed from the top of the bed.

2. The process of claim 1; wherein the step of providing provides two adsorption beds in a pressure swing adsorption system.

3. The process of claim 1, wherein the ratio of the purge phase time to the adsorption phase time is greater than 0.2.

4. The process of claim 1, wherein the feedstream temperature is greater than 300 degrees Fahrenheit.

5. The process of claim 1, wherein the ratio of first pressure to second pressure is greater than 10.

6. The process of claim 5, wherein the first pressure is less than 25 psia and the second pressure is less than 2.5 psia.

7. The process of claim 1, wherein the step of reducing the pressure and contacting the dehydrated alcohol stream produce an exhaust stream that is directed to a distillation column.

8. The process of claim 1, wherein the feedstream comprises less than 10 wt. % water.

9. The process of claim 6, wherein the step of reducing pressure and the step of increasing pressure has a rate of pressure change that is greater than 30 psi per minute.

10. The process of claim 1, wherein the C 1-4 alcohol is ethanol.

* * * * *